United States Patent
Ghosh

(10) Patent No.: US 9,272,148 B2
(45) Date of Patent: Mar. 1, 2016

(54) COMBINATION OF FEEDBACK ON MECHANICAL AND ELECTRICAL RESYNCHRONIZATION TO SELECT THERAPY PARAMETERS

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/948,831

(22) Filed: Jul. 23, 2013

(65) Prior Publication Data

US 2015/0032174 A1 Jan. 29, 2015

(51) Int. Cl.
 A61N 1/36 (2006.01)
 A61N 1/365 (2006.01)
 A61N 1/362 (2006.01)
 A61N 1/372 (2006.01)

(52) U.S. Cl.
 CPC ............ *A61N 1/36585* (2013.01); *A61N 1/362* (2013.01); *A61N 1/36185* (2013.01); *A61N 1/372* (2013.01)

(58) Field of Classification Search
 CPC ........... A61B 5/04011; A61B 5/04012; A61B 5/0452; A61B 5/0456; A61B 5/0472
 USPC ......................................... 600/503, 508–527
 See application file for complete search history.

(56) References Cited

U.S. PATENT DOCUMENTS

| | | | |
|---|---|---|---|
| 6,418,346 B1 | 7/2002 | Nelson | |
| 6,442,433 B1 | 8/2002 | Linberg | |
| 6,473,638 B2 | 10/2002 | Ferek-Petric | |
| 6,480,745 B2 | 11/2002 | Nelson | |
| 6,599,250 B2 | 7/2003 | Webb | |
| 6,804,555 B2 | 10/2004 | Warkentin | |
| 7,092,759 B2 | 8/2006 | Nehls | |
| 7,308,297 B2 | 12/2007 | Reddy | |
| 7,308,299 B2 | 12/2007 | Burrell | |
| 7,587,074 B2 | 9/2009 | Zarkh | |
| 7,610,088 B2 | 10/2009 | Chinchoy | |

(Continued)

FOREIGN PATENT DOCUMENTS

| | | |
|---|---|---|
| WO | 2005089867 A1 | 9/2005 |
| WO | 2006105474 A3 | 10/2007 |

(Continued)

OTHER PUBLICATIONS (PCT/US2014/047632) PCT Notification of Transmittal of the International Search Report and the Written Opinion of the International Searching Authority.

(Continued)

*Primary Examiner* — Paula J Stice
(74) *Attorney, Agent, or Firm* — Carol F. Barry

(57) ABSTRACT

A system and method select a pacing site for a cardiac pacing therapy. A change from a baseline mechanical activity is extracted from a signal of mechanical heart activity during pacing at each one of multiple pacing sites along a heart chamber. A change from a baseline electrical activity is extracted from a signal of electrical heart activity during pacing at each of the of pacing sites. The pacing sites are sorted in a first order based upon the changes in mechanical heart activity and in a second order based upon the changes in electrical heart activity. A pacing site is selected from the multiple pacing sites as a common pacing site between the first order and the second order.

22 Claims, 4 Drawing Sheets

(56) References Cited

U.S. PATENT DOCUMENTS

| | | |
|---|---|---|
| 7,613,500 B2 | 11/2009 | Vass |
| 7,844,335 B2 | 11/2010 | Lippert |
| 7,917,214 B1 | 3/2011 | Gill et al. |
| 7,941,213 B2 | 5/2011 | Markowitz |
| 8,036,743 B2 | 10/2011 | Savage |
| 8,050,760 B2 | 11/2011 | Cholette |
| 8,145,308 B2 | 3/2012 | Sambelashvili |
| 8,150,513 B2 | 4/2012 | Chinchoy |
| 8,160,700 B1 | 4/2012 | Ryu et al. |
| 8,180,428 B2 | 5/2012 | Kaiser |
| 8,527,049 B2 | 9/2013 | Koh et al. |
| 2003/0083709 A1 | 5/2003 | Zhu et al. |
| 2004/0015081 A1 | 1/2004 | Kramer |
| 2004/0215253 A1 | 10/2004 | Weinberg |
| 2005/0090870 A1 | 4/2005 | Hine et al. |
| 2006/0235289 A1 | 10/2006 | Wesselink |
| 2007/0150009 A1 | 6/2007 | Kveen |
| 2008/0021336 A1 | 1/2008 | Dobak |
| 2008/0183072 A1 | 7/2008 | Robertson |
| 2008/0242976 A1 | 10/2008 | Robertson |
| 2009/0043352 A1 | 2/2009 | Brooke et al. |
| 2009/0099619 A1 | 4/2009 | Lessmeier |
| 2009/0157136 A1 | 6/2009 | Yang |
| 2009/0318995 A1 | 12/2009 | Keel |
| 2010/0042174 A1 | 2/2010 | Koh et al. |
| 2010/0145405 A1 | 6/2010 | Min et al. |
| 2010/0152801 A1 | 6/2010 | Koh et al. |
| 2010/0268059 A1 | 10/2010 | Ryu et al. |
| 2011/0022112 A1 | 1/2011 | Min |
| 2011/0066201 A1 | 3/2011 | Rosenberg et al. |
| 2011/0098772 A1 | 4/2011 | Min |
| 2011/0118803 A1 | 5/2011 | Hou |
| 2011/0137369 A1 | 6/2011 | Ryu et al. |
| 2011/0319953 A1 | 12/2011 | Reed et al. |
| 2011/0319954 A1 | 12/2011 | Niazi et al. |
| 2012/0109244 A1* | 5/2012 | Anderson et al. ............... 607/17 |
| 2012/0283587 A1 | 11/2012 | Gosh |
| 2012/0284003 A1 | 11/2012 | Gosh |
| 2012/0310296 A1 | 12/2012 | Noren |
| 2013/0116739 A1 | 5/2013 | Brada |
| 2014/0371832 A1 | 12/2014 | Ghosh |

FOREIGN PATENT DOCUMENTS

| | | |
|---|---|---|
| WO | 2009079344 A4 | 9/2009 |
| WO | 2010052303 A1 | 5/2010 |
| WO | 2012061612 A2 | 5/2012 |

OTHER PUBLICATIONS

U.S. Appl. No. 13/916,353, filed Jun. 12, 2013.

\* cited by examiner

COMBINATION OF FEEDBACK ON MECHANICAL AND ELECTRICAL RESYNCHRONIZATION TO SELECT THERAPY PARAMETERS

TECHNICAL FIELD

The disclosure relates generally to optimizing therapy control parameters during cardiac pacing therapies and more particularly to optimizing therapy control parameters based on both mechanical and electrical heart activity feedback.

BACKGROUND

Cardiac resynchronization therapy (CRT) is a treatment for heart failure patients in which one or more heart chambers are electrically stimulated (paced) to restore or improve heart chamber synchrony. Improved heart chamber synchrony is expected to improve hemodynamic performance of the heart, such as assessed by ventricular pressure and the rate of change in ventricular pressure or other hemodynamic parameters, thereby alleviating symptoms of heart failure. Achieving a positive clinical benefit from CRT is dependent on several therapy control parameters, such as the atrio-ventricular (AV) delay, inter-ventricular (VV) delay and pacing site(s). The AV delay controls the timing of ventricular pacing pulses relative to an atrial depolarization, intrinsic or paced. The VV delay controls the timing of a pacing pulse in one ventricle relative to a paced or intrinsic sensed event in the other ventricle. Pacing may be delivered in the right ventricle and/or the left ventricle.

Numerous methods for selecting optimal therapy parameters for delivering CRT pacing pulses have been proposed. For example, clinicians may select an optimal AV or VV delay using Doppler echocardiography or other imaging modalities to optimize a hemodynamic variable. Other methods may be based on a hemodynamic sensor signal or a sensor of mechanical heart function included in or coupled to the implantable medical device.

However, signals from mechanical sensors or imaging techniques may have a high degree of variability. For example, evaluation of mechanical ventricular dyssynchrony by echocardiographic methods may have both intra- and inter-operator variability. Moreover, signals from mechanical sensors may be influenced by several factors independent of CRT, such as dosage of medication, anesthetics for intraoperative evaluation, etc., which modulate the contractility and mechanical motion of the heart. Evaluation of signals from mechanical sensors often involve some method of signal averaging over multiple cardiac events and hence influenced by variations that may be present from one cardiac event to another, such as frequent ventricular ectopy interfering with CRT, which makes the effect of pacing alone difficult to isolate.

Analysis of multiple parameters detected from an implantable cardiac device for assessing heart failure projection is generally disclosed in pre-grant U.S. Publication No. 2012/0109244 (Anderson, et al.). The parameters may include mechanical synchrony, electrical synchrony, and/or electromechanical delay. A multi-polar lead is disclosed and may be used for acquiring signals for this analysis. The analysis may be the basis for modifying pacing delays (for example AV or VV delays) and thus are used to adjust the timing of pacing pulses but without consideration of pacing site. Pacing site selection for CRT is not addressed, yet pacing site selection may be critical to achieving positive patient response to CRT.

SUMMARY

In general, the disclosure is directed towards techniques for selecting a pacing site for delivering a cardiac pacing therapy. In some examples, pacing site selection is based on a combination of an index of mechanical synchrony and an index of electrical synchrony of the ventricles.

In one embodiment, a method for selecting a pacing site includes extracting from a signal of mechanical heart activity a change from a baseline mechanical activity during pacing at different pacing sites along a heart chamber and extracting from a signal of electrical heart activity a change from a baseline electrical activity during pacing at each of the pacing sites. The pacing sites are sorted in one list based upon the changes in mechanical heart activity and in another list based upon the changes in electrical heart activity. A common pacing site between the sorted first order and the sorted second order is selected or recommended as a pacing site for delivering therapy. In some embodiments, the pacing site is a selected as a site having a highest overall ranking in the first and second lists. A pacing site may be eliminated from a list if it does not result in a threshold improvement in mechanical or electrical synchrony.

In another example, a system for selecting a pacing site includes multiple electrodes for producing a signal of electrical heart activity and for delivering cardiac pacing pulses to pacing sites along a heart chamber and a sensor for producing a signal of mechanical heart activity. During pacing at each of the pacing sites one at a time, a processor extracts a change from a baseline mechanical activity from the signal of mechanical heart activity and a change from a baseline electrical activity, from the signal of electrical heart activity. The processor sorts the pacing sites in a first order based upon the changes in mechanical heart activity and in a second order based upon the changes in electrical heart activity. The processor selects a therapy delivery pacing site from the pacing sites as a common pacing site between the sorted first order and the sorted second order.

In another example a non-transitory, computer-readable storage medium includes instructions that, when executed, cause a processor to extract a change from a baseline mechanical activity from a signal of mechanical heart activity during pacing delivered to multiple test pacing sites one at a time, extract a change from a baseline electrical activity from a signal of electrical heart activity during the pacing delivered to the multiple test pacing sites, sort the pacing sites in a first order based upon the changes in mechanical heart activity and in a second order based upon the changes in electrical heart activity, and select a pacing site for therapy delivery as a common pacing site between the first order and the second order.

The details of one or more aspects of the disclosure are set forth in the accompanying drawings and the description below. Other features, objects, and advantages will be apparent from the description and drawings, and from the claims.

DETAILED DESCRIPTION

Fundamentally, CRT alters electrical activation of the ventricles, improving spatial synchronization of electrical conduction in hearts with electrical conduction disorders such as left bundle branch block, right bundle branch block or other disorders. Optimal electrical activation of the heart may therefore be important for CRT efficacy. Optimal electrical activation can depend on a number of factors including the location of the pacing electrodes and pacing timing parameters such as AV delay and VV delay. Techniques disclosed herein enable an IMD to perform pacing site analysis for automatic or recommended pacing site selection for delivering CRT.

Restoration of electrical synchrony may be associated with chronic patient response to CRT. A reduction in electrical dyssynchrony during CRT can have a strong correlation with direct measures of hemodynamics, e.g. as obtained by measurement of LV pressure with a pressure catheter during intraoperative biventricular pacing. Valid signals of electrical dyssynchrony may be obtained during a single cardiac cycle. Evaluation of electrical dyssynchrony during a single cardiac cycle can isolate the effects of CRT from other confounding events like ventricular ectopy. An optimal pacing site for CRT may be one that provides resynchronization of both electrical heart activity and mechanical heart activity. As disclosed herein, a scheme for selection of optimal CRT pacing site(s) is based on a combined analysis of two separate measures of cardiac activity including both electrical and mechanical indices of ventricular synchrony, thereby achieving greater fidelity in assessing the CRT response and a reduced sensitivity to confounding factors.

Figure 1:
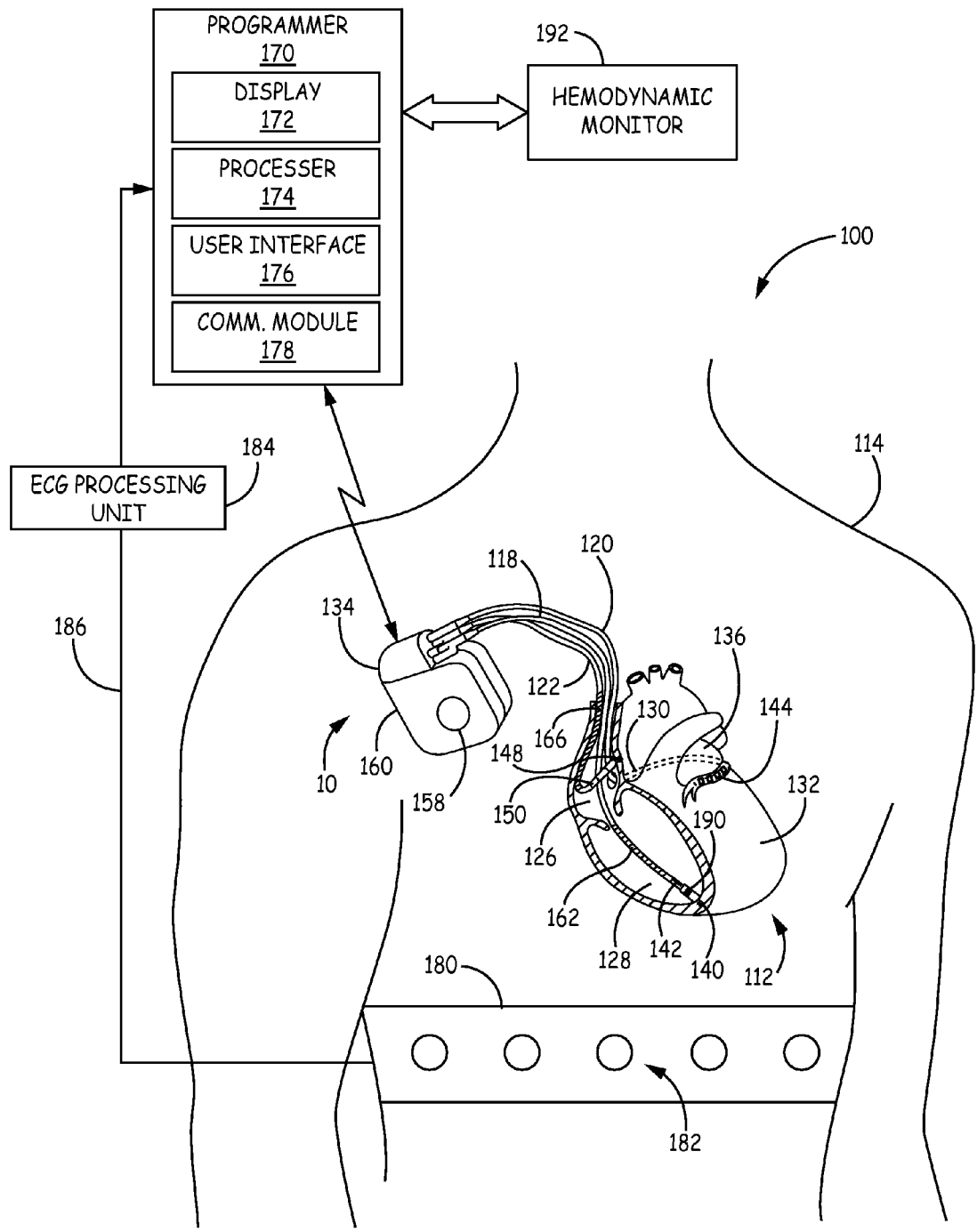
FIG. 1 is a schematic diagram of one embodiment of an implantable medical device (IMD) system in which techniques disclosed herein may be implemented.

FIG. 1 is a schematic diagram of one embodiment of an implantable medical device (IMD) system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, and deliver high voltage cardioversion or defibrillation therapy to heart 112 in the form of electrical shock pulses. Pacing and sensing of the cardiac chambers is typically achieved using the pace/sense electrodes 140, 142, 144 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location.

IMD 10 includes internal circuitry for performing the functions attributed to IMD 10. Housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT by delivering pacing pulses in one or both ventricles 128 and 132 for controlling and improving ventricular synchrony. LV pacing may be delivered using a selected pacing vector that utilizes at least one electrode 144 on multipolar LV lead 120. RV pacing is delivered using RV tip electrode 140 and ring electrode 142. CRT may be delivered by pacing in a single ventricular chamber (LV or RV) or both chambers (biventricular pacing) depending on patient need. The methods described herein are implemented in a dual or multi-chamber pacemaker or ICD delivering pacing pulses to the right and/or left ventricles using programmable pacing pulse timing parameters and selected pacing vectors.

In some embodiments, IMD 10 is configured to provide "adaptive CRT" which automatically switches between biventricular pacing and LV-only pacing in response to changes in the patient's intrinsic AV conduction. When AV conduction is impaired or blocked, or more generally when AV conduction time is slowed, biventricular pacing is delivered. When normal AV conduction returns, LV-only pacing is delivered. In this way, RV pacing is delivered only when needed based on the patient's own AV conduction status, which may fluctuate over time. Pacing sites selected using the techniques described herein may automatically be selected as IMD 10 switches between biventricular pacing and LV-only pacing, which may include selection of different pacing sites in the LV for biventricular pacing than for LV-only pacing.

While a multi-chamber ICD is shown in FIG. 1, it is recognized that techniques disclosed herein may be implemented in a single chamber, dual chamber or multi-chamber pacemaker, with or without anti-arrhythmia therapies such as cardioversion and defibrillation shock capabilities. Other examples of implantable devices which techniques disclosed herein may be implemented, in whole or in part, are generally disclosed in pre-grant U.S. Publication No. 2007/0150009 (Kveen) and pre-grant U.S. Publication 2012/0310296

(Noren). Techniques disclosed herein for CRT optimization may be used to select an optimal pacing site, which may include RV pacing site(s) and/or LV pacing site(s) and may further include selecting optimal pacing timing parameter(s). As will be described herein, baseline data of mechanical heart activity and baseline data of electrical heart activity are collected during no ventricular pacing. CRT is delivered using different test pacing sites to record mechanical heart activity and electrical heart activity data for each test pacing site. The different pacing sites may be along a single multi-polar lead carrying electrodes positioned along a single cardiac chamber or multiple leads positioned along one or more cardiac chambers. Proportional changes from the baseline data of the mechanical and electrical data for each of the different pacing sites are determined. The pacing sites are ordered based upon these proportional changes to guide pacing site selection for delivering CRT.

In some embodiments, mechanical heart activity data may be obtained using an external hemodynamic monitoring or imaging device 192, such as an external blood pressure monitor, flow monitor, heart sound monitor or echocardiography, fluoroscopy or other imaging device. The external device 192 may be wholly external or coupled to a catheter or other transcutaneous, transvenous, or subcutaneous device for producing a signal of mechanical heart activity. An external hemodynamic monitoring device 192 for acquiring mechanical heart activity data may transfer data to external programmer 170 or another external processing device for use in a pacing site selection algorithm.

In other embodiments, mechanical heart activity data may be obtained using an implantable sensor included in or coupled to IMD 10. In the embodiment shown in FIG. 1, a hemodynamic sensor 190 is carried by lead 118 for producing a signal of mechanical heart activity provided to a processor in IMD 10. Sensor 190 may be embodied, for example, as a pressure sensor, heart sound sensor, or accelerometer. One or more leads 118, 120, and 122 and/or housing 160 may include a sensor of mechanical heart activity for producing signals correlated to the motion of the heart or blood for determining a mechanical or hemodynamic effect of CRT. Other techniques for determining a change in mechanical heart activity from a baseline mechanical heart activity may involve direct or indirect measures of cardiac output, cardiac contractility, left ventricular ejection fraction, or cardiac motion using mechanical sensors and/or imaging techniques. Various examples of techniques that may be implemented for use in determining a change in mechanical heart activity are generally disclosed in commonly-assigned U.S. Pat. No. 7,941,213 (Markowitz), U.S. Pat. No. 6,473,638 (Ferek-Petric), U.S. Pat. No. 7,092,759 (Nehls), U.S. Pat. No. 7,610,088 (Chinchoy), U.S. Pat. No. 8,150,513 (Chinchoy), and U.S. Pat. No. 8,180,428 (Kaiser), all of which patents are incorporated herein by reference in their entirety. Imaging techniques can include techniques for tracking motion of cardiac leads. Reference is made, for example, to commonly assigned pre-grant U.S. Publication No. 2006/0235289 (Wesselink), hereby incorporated herein by reference in its entirety and to U.S. Publication No. 2009/0099619 (Lessmeier et al.).

Electrical activity data may be obtained by sensing electrical signals at any of electrodes 140, 142, 144, 148, 150, 158, 162, and 166. Additionally or alternatively, electrical activity data may be obtained using external surface electrodes. In some examples, system 100 includes an array of surface electrodes 182, which may be carried by a belt or strap 180 adapted to be wrapped around the torso of patient 114 to position electrodes 182 in the vicinity of heart 112. Strap 180 is shown inferior to heart 112 in FIG. 1, but it is understood that belt 180 may be positioned in a relatively more superior position to surround heart 112 such that electrodes 180 are positioned nearer to heart 112. Electrodes 182 are used to acquire surface potential signals from heart 112 for use in CRT pacing site selection in some embodiments.

Electrodes 182 may be positioned around the circumference of patient 114, including the posterior, lateral, and anterior surfaces of the torso of patient 114. In other examples, electrodes 182 may be positioned on any one or more of the posterior, lateral, and anterior surfaces of the torso. Electrodes 182 may be electrically connected to an ECG processing unit 184 via a wired connection 186. Some configurations may use a wireless connection to transmit the signals sensed by electrodes 182 to ECG processing unit 184, e.g., as channels of data.

Although in the example of FIG. 1, strap 180 is shown carrying surface electrodes 182, in other examples any of a variety of mechanisms, e.g., tape or adhesives, may be employed to aid in the spacing and placement of electrodes 182 relative to heart 112. In some examples, strap 180 may include an elastic band, strip of tape, or cloth. In some examples, electrodes 182 may be placed individually on the torso of patient 114.

Electrodes 182 may surround heart 112 of patient 114 and record the electrical signals associated with the depolarization and repolarization of heart 112. Each of electrodes 182 may be used in a unipolar configuration to sense the surface potentials that reflect the cardiac signals. ECG processing unit 184 may also be coupled to a return or indifferent electrode (not shown) which may be used in combination with each of electrodes 182 for unipolar sensing. In some examples, there may be 12 to 16 electrodes 182 spatially distributed around the torso of patient 114. Other configurations may have more or fewer electrodes 182.

ECG processing unit 184 may record and analyze the surface potential signals, referred to generally herein as "ECG" signals, sensed by electrodes 182. Processing unit 184 may be configured to provide an index to programmer 170 based on electrical heart activity and indicating electrical dyssynchrony of heart 112. Programmer 170 may use data obtained from hemodynamic monitor 192, ECG processing unit 184, and/or IMD 10 for use in automatically selecting or generating a notification to a clinician of a recommended pacing site(s) for delivering CRT. Alternatively, a processor included in IMD 10 may receive the mechanical activity data and the electrical activity data and perform the processing steps for identifying a pacing site for therapy delivery.

In one example, ECG processing unit 184 may compute activation times directly from sensed surface potential signals. An activation time for each electrode location (of electrodes 182) may be determined as a time period between two events, such as between the QRS complex onset and the minimum derivative during the QRS signal (i.e., the steepest negative slope of the sensed potential signal) at the respective electrode. Values of one or more indices indicative of the temporal and/or spatial distribution of the activation times may be determined as measures or indicators of electrical dyssynchrony. These indicators of electrical dyssynchrony may be used to evaluate change from baseline electrical activity during CRT applied at different test pacing sites.

Examples of indices of cardiac electrical dyssynchrony that may be calculated from surface potential signals sensed by electrodes 182 include a standard deviation of the determined activation times, a range of activation times, and a percentage of late activations. All or a subset of the surface electrodes (e.g., only electrodes located on the left anterior, left lateral and left posterior regions of the torso) may be used for calculation or computation of the activation times. The range of activation times may be computed as the difference between the maximum and the minimum cardiac activation times determined from all or a subset of electrodes 182. The percentage of late activations estimates the percentage of electrodes 182 whose associated activation times are greater than a certain percentile, for example the $70^{th}$ percentile, of the QRS complex duration or the determined activation times for electrodes 182. Techniques for determining indices of electrical dyssynchrony based on surface activation times are generally disclosed in commonly-assigned pre-grant U.S. Patent Publication No. 2012/0283587 A1 (Ghosh, et al.) hereby incorporated herein by reference in its entirety. Indices of electrical dyssynchrony derived from external surface ECG leads are generally described, which may be used for determining a change in electrical heart activity from a baseline.

CRT pacing site selection based on such electrical activity data derived from surface ECG leads and/or implanted electrodes and mechanical activity data derived from external hemodynamic monitor 192 and/or implanted sensor(s) 190 can be performed at implant or at patient follow-up visits. Other electrical signal recording apparatus and techniques that may be used to obtain electrical heart activity data in a clinical setting may include 12-lead ECG electrodes, a vest carrying an array of electrodes, and vectorcardiography. Automatic CRT pacing site selection based on electrical and mechanical activity data derived from implanted electrodes 140, 142, 144, 148, 150, 158, 162 and 166 and implanted sensor 190 may be performed periodically by IMD 10.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD. A user interacting with programmer 170 can initiate a CRT optimization procedure performed by IMD 10 automatically or semi-automatically, to establish data for CRT pacing site selection.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, or MICS, for example. In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote monitoring and management of patient 114 using the techniques described herein. Remote patient management systems may be configured to utilize the presently disclosed techniques to enable a clinician to review CRT therapy parameters and authorize programming of IMD 10. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are hereby incorporated herein by reference in their entirety.

Figure 2:
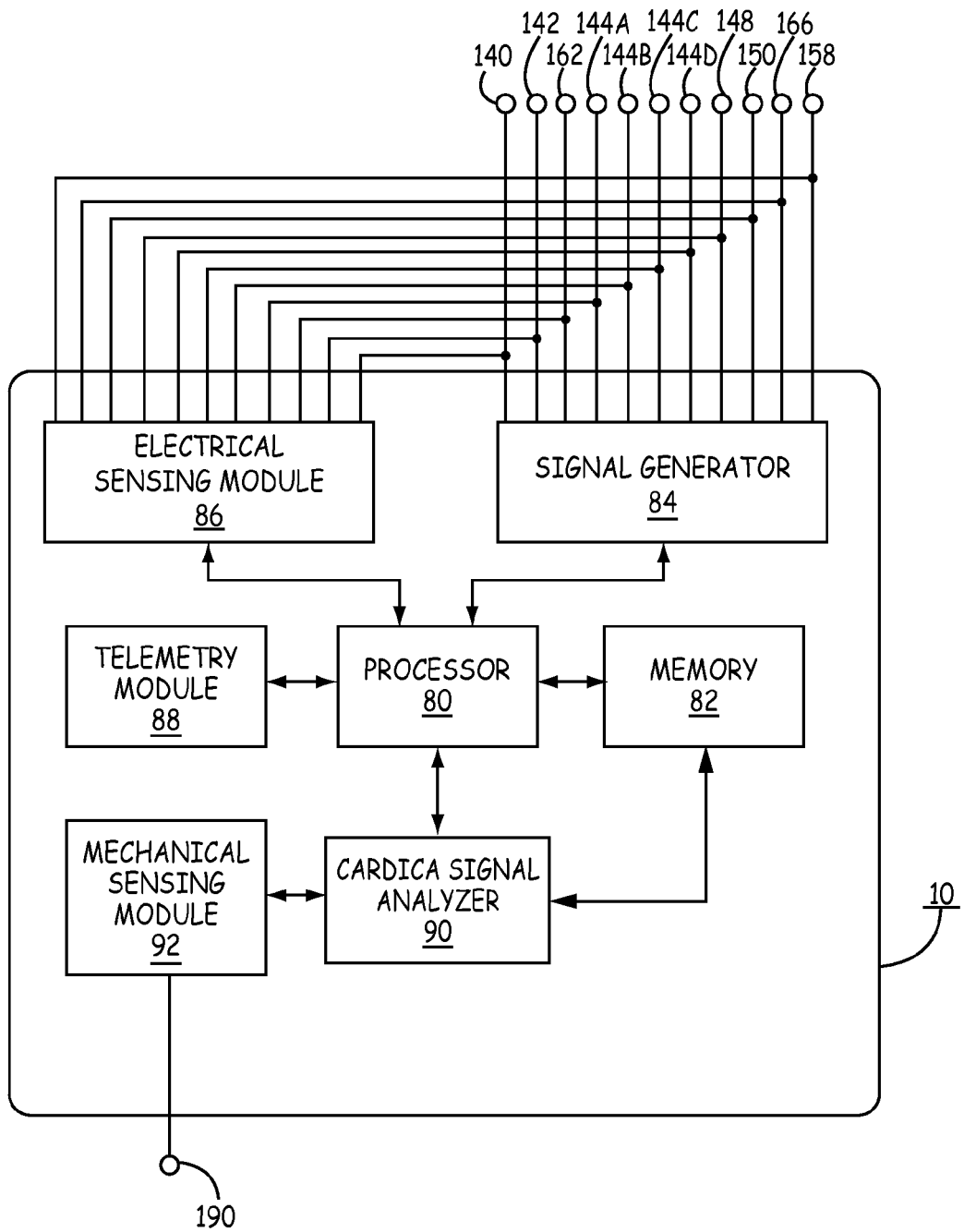
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, also referred to herein as "processor" 80, memory 82, signal generator 84, electrical sensing module 86, mechanical sensing module 92, and telemetry module 88. IMD 10 further includes cardiac signal analyzer 90 receiving signals from electrical sensing module 86 and mechanical sensing module 92.

Memory 82 may include computer-readable instructions that, when executed by processor 80, cause IMD 10 and processor 80 to perform various functions attributed throughout this disclosure to IMD 10, processor 80, and cardiac signal analyzer 90. The computer-readable instructions may be encoded within memory 82. Memory 82 may comprise non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory propagating signal.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, cardiac signal analyzer 90 may, at least in part, be stored or encoded as instructions in memory 82 that are executed by processor and control unit 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. A pacing electrode site is selected based on an analysis of mechanical heart activity and electrical activity by cardiac signal analyzer 90 as will be described herein. Signal generator 84 delivers cardiac pacing pulses according to AV and/or VV delays during CRT. These delays may be set based on an analysis of cardiac signals by analyzer 90.

Signal generator 84 may include a switch module (not shown) and processor and control unit 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors cardiac electrical signals for sensing cardiac electrical events, e.g. P-waves and R-waves, from selected ones of electrodes 140, 142, 144A-144D, 148, 150, 158, 162, or 166 in order to monitor electrical activity of heart 112. Sensing module 86 may also include a switch module to select which of the available electrodes are used to sense the cardiac electrical activity. In some examples, processor 80 selects the electrodes to function as sense electrodes, or the sensing vector, via the switch module within sensing module 86.

Sensing module 86 includes multiple sensing channels, each of which may be selectively coupled to respective combinations of electrodes 140, 142, 144A-144D, 148, 150, 158, 162, or 166 to detect electrical activity of a particular chamber of heart 112. Each sensing channel may comprise an amplifier that outputs an indication to processor 80 in response to sensing of a cardiac depolarization, in the respective chamber of heart 112. In this manner, processor 80 may receive sense event signals corresponding to the occurrence of R-waves and P-waves in the various chambers of heart 112, e.g. ventricular sense events and atrial sense events corresponding to intrinsic depolarization of the respective heart chamber. Sensing module 86 may further include digital signal processing circuitry for providing processor 80 or cardiac signal analyzer 90 with digitized EGM signals.

The occurrence of R-waves in the ventricles, e.g. in the RV, may be used in monitoring intrinsic AV conduction time. In particular, prolongation of the AV conduction time or the detection of AV block based on R-wave sensing during no ventricular pacing (or pacing at an extended AV delay that allows intrinsic conduction to take place) is used to control adaptive CRT in some embodiments. When AV conduction is impaired, signal generator 84 is controlled by processor 80 to deliver biventricular pacing, i.e. pacing pulses are delivered in the RV and the LV using a selected AV delay and a selected VV delay and selected LV pacing site(s) using one or more of electrodes 144. When AV conduction is intact, signal generator 84 is controlled by processor 80 to deliver LV-only pacing at a selected LV pacing site to optimally improve both mechanical and electrical ventricular synchrony.

As described herein, the LV pacing site may be optimized uniquely for different heart rhythm states such as rhythm states involving atrial sensing, atrial pacing, LV-only pacing, or biventricular pacing. For example, four distinct atrioventricular rhythm states may be evaluated: 1) atrial-sensed, biventricular paced 2) atrial-paced, biventricular paced 3) atrial-sensed, LV-only paced and 4) atrial-paced, LV-only paced. Mechanical and electrical heart activity data may be established for different rhythm states and used to adjust the LV pacing site according to the data and the current atrial sensing or pacing rhythm state and/or LV-only or biventricular pacing state.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event in another chamber. Memory 82 stores CRT control parameters such as AV and VV delays and selected pacing site(s).

In some embodiments, IMD 10 includes a mechanical sensing module 92 for receiving a signal from sensor 190, which may be embodied as a pressure sensor, accelerometer, acoustical sensor, or other sensor of mechanical heart activity. Sensor 190 may be coupled to IMD 10 via a lead and necessary feedthroughs. Alternatively, sensor 190 may be incorporated within or along housing 160. In still other embodiments, a mechanical heart activity sensor may be embodied as a wireless implantable sensor capable of transmitting data signals to telemetry module 88. Mechanical sensing module 92 may filter and amplify received mechanical signals and provide cardiac signal analyzer 90 with analog and/or digitized signals of mechanical heart activity.

Cardiac signal analyzer 90 receives electrical cardiac signals from sensing module 86 and mechanical cardiac signals from sensing module 92 to evaluate the electrical synchrony and the mechanical synchrony of the right and left ventricles. An index of mechanical synchrony and an index of electrical synchrony are determined by cardiac signal analyzer during a baseline condition (no ventricular pacing) and during ventricular pacing at multiple test pacing sites. These indices of mechanical and electrical synchrony are stored in memory 82 and used for selecting a pacing site for delivering therapy.

Other examples of functional block diagrams (FIGS. 3A-3B) of IMD 10 may be seen with respect to U.S. patent application Ser. No. 13/916,353 filed Jun. 12, 2013, and assigned to the assignee of the present invention, the disclosure of which is incorporated by reference in its entirety herein.

Figure 3:
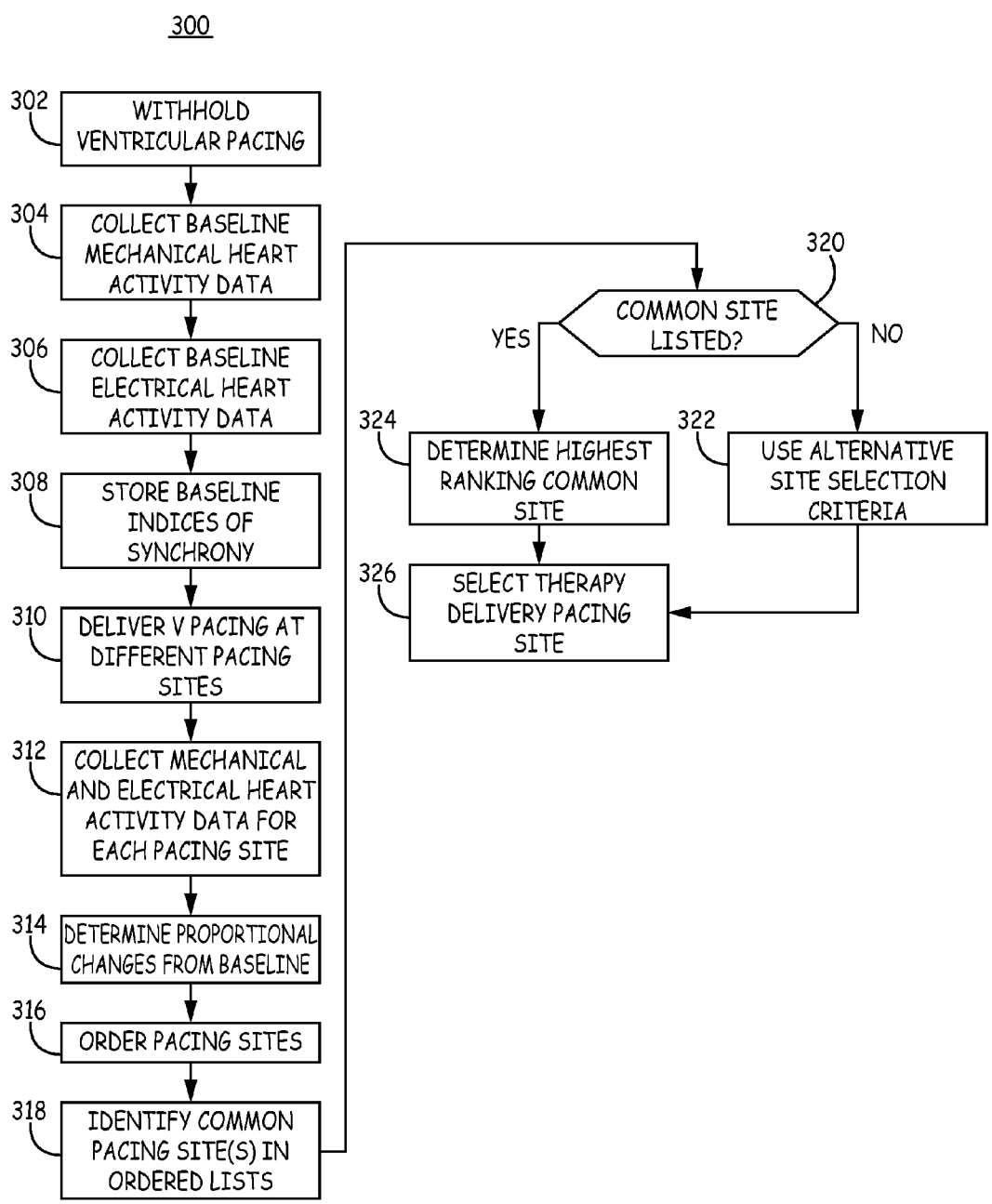
FIG. 3 is a flow chart of a method for selecting a pacing site for delivering a pacing therapy, such as CRT.

FIG. 3 is a flow chart 300 of a method for selecting a pacing site for delivering a pacing therapy, such as CRT. In the following description, the method shown by flow chart 300 is performed by processor 80 and cardiac signal analyzer 90 using signals from sensing modules 86 and 92. Alternatively, the method may be performed by an external processing device, such as processor 174 of external programmer 170 using signals received from IMD 10, hemodynamic monitor 192 and/or ECG processing unit 184. At block 302, ventricular pacing is withheld to enable collection of baseline data at blocks 304 and 306. The heart rhythm may be an atrial paced rhythm or an atrial sensed rhythm during collection of baseline data. In some embodiments, baseline data may be collected for both an atrial paced and an atrial sensed rhythm to enable separate identification of an optimal pacing site to be for used during atrial pacing and during atrial sensing.

The mechanical heart activity data collected at block 304 is used by cardiac signal analyzer 90 to determine a baseline index of mechanical synchrony of the ventricles. This baseline index may be a peak amplitude, peak-to-peak difference, slope, area, time interval or other feature measured from a hemodynamic signal such as a blood pressure signal, blood flow signal, heart sound signal, or heart wall motion signal. As described previously, the mechanical heart activity data may be collected using an external monitor or imaging device and/or an implantable sensor.

The electrical heart activity data collected at block 306 is used by cardiac signal analyzer 90 to determine a baseline index of electrical synchrony of the ventricles. This baseline index may be a feature, e.g. a peak amplitude, signal width, peak-to-peak difference, slope, or time interval between two fiducial points, derived from an EGM signal sensed by implanted electrodes. In some embodiments, a baseline index may be derived from ECG signals acquired from external skin electrodes or a combination of EGM and ECG signals.

When extracting an index of mechanical or electrical heart synchrony, one or more cardiac cycles may be used to determine a statistical mean, median mode or other statistical aspect of the respective signal. In some examples, multiple cycles are ensemble averaged. In some embodiments, an index of electrical heart activity is extracted from a single cardiac cycle to eliminate confounding factors such as ectopic beats. When extracting the index from a single beat, the beat may be prospectively verified as being a successfully paced beat in which the delivered biventricular or LV-only pacing pulse(s) have captured the ventricle(s). Verification of the paced beat may be performed by evaluating the ECG or EGM morphology, for example.

The derived baseline mechanical and electrical indices of synchrony during no ventricular pacing are stored in memory at block 308. At block 310, a pacing therapy is delivered at multiple test pacing sites, one at a time in a sequential manner, to enable collection of mechanical and electrical heart activity data at block 312 during pacing at each respective pacing site. The ventricular pacing may be delivered at a nominal AV delay or at an AV delay previously optimized, e.g. using echocardiography or other techniques.

In the illustrative embodiment, CRT is delivered using each LV pacing electrode included on a multi-polar lead, such as electrodes 144 of quadrapolar lead 120. The LV electrodes 144 may be paired one at a time with a common anode, e.g. the IMD housing electrode 158 or a coil electrode 162 or 166 to deliver unipolar pacing to the LV during successive intervals of time at each of the pacing sites corresponding to electrodes 144. During each pacing interval at each test pacing site, the mechanical and electrical heart activity data is collected to enable cardiac signal analyzer to extract an index of mechanical synchrony and an index of electrical synchrony for each test pacing site.

In some embodiments, pacing may be delivered at each pacing site individually and at combinations of two or more pacing sites at block 310. Some patients may experience clinically significant benefit from multi-site pacing in the LV during CRT. Accordingly, LV electrodes 144 may be selected one at time, two at a time, or even three at a time during episodes of pacing for collecting mechanical and electrical cardiac activity data at block 312 for each pacing site individually and various combinations of pacing sites during multi-site pacing in the LV.

In some embodiments, indices of mechanical and electrical synchrony may be acquired for each LV pacing site during LV-only pacing and during biventricular pacing. An optimal LV pacing site may be separately determined for use during LV-only pacing and during biventricular pacing. During biventricular pacing, pacing is delivered to the RV using pacing electrodes 140 and 142, for example, and a VV delay is used to control the timing between the RV pacing pulse and the LV pacing pulse delivered at a test site. A nominal VV delay may be used, e.g. a 0 ms VV delay. Alternatively, different test VV delay settings may be applied during pacing at each test LV pacing site to determine mechanical and electrical synchrony indices for each test episode, defined by a test VV delay setting and a test LV pacing site or combination of LV pacing sites (if multi-site pacing is also being tested).

At block 314, the indices of mechanical and electrical synchrony determined for each test episode are compared to the baseline indices stored in memory. A proportional change from baseline is determined for each test episode. The change may be a positive or negative percentage change from baseline and the percentage change may be an improvement in synchrony or a worsening in synchrony. An improvement in synchrony may correspond to a positive or a negative percentage change in a given index depending on the particular index being used. For example, if an index relating to left ventricular chamber pressure measurement is being used as a mechanical synchrony index, a positive percentage change (i.e. an increase) in the index may indicate an improvement in mechanical synchrony. If an index relating to QRS width is being used as an electrical synchrony index, a negative percentage (i.e. a decrease) in the index may indicate an improvement in electrical synchrony.

At block 316, the pacing sites are ordered according to the proportional changes form baseline. The pacing sites are sorted in one ordered list according to proportional changes of the mechanical synchrony index from baseline and in a second ordered list according to proportional changes of the electrical synchrony index from baseline. The sorting to produce each ordered list is done based upon improvement in the respective synchrony index during pacing. In some embodiments, prior to ordering the pacing sites, pacing sites that do not meet a threshold improvement from baseline are rejected and not included in the listing.

For example, pacing sites resulting in a worsening of a mechanical synchrony index relative to baseline may be rejected from the list ordering the pacing sites according to proportional change in mechanical synchrony. Likewise, a pacing site resulting in a worsening in electrical synchrony from baseline may be eliminated form a list ordering the pacing sites according to proportional change in electrical synchrony. After ordering the pacing sites, pacing sites common to each list are identified at block 318 as candidate pacing sites for therapy delivery.

Ordering the pacing sites may include ordering each test episode when different VV delays are used at each pacing site. Alternatively, test pacing sites may be ordered for a nominal VV delay, and then VV delay may be optimized subsequent to selecting an optimal pacing site.

Figure 4:
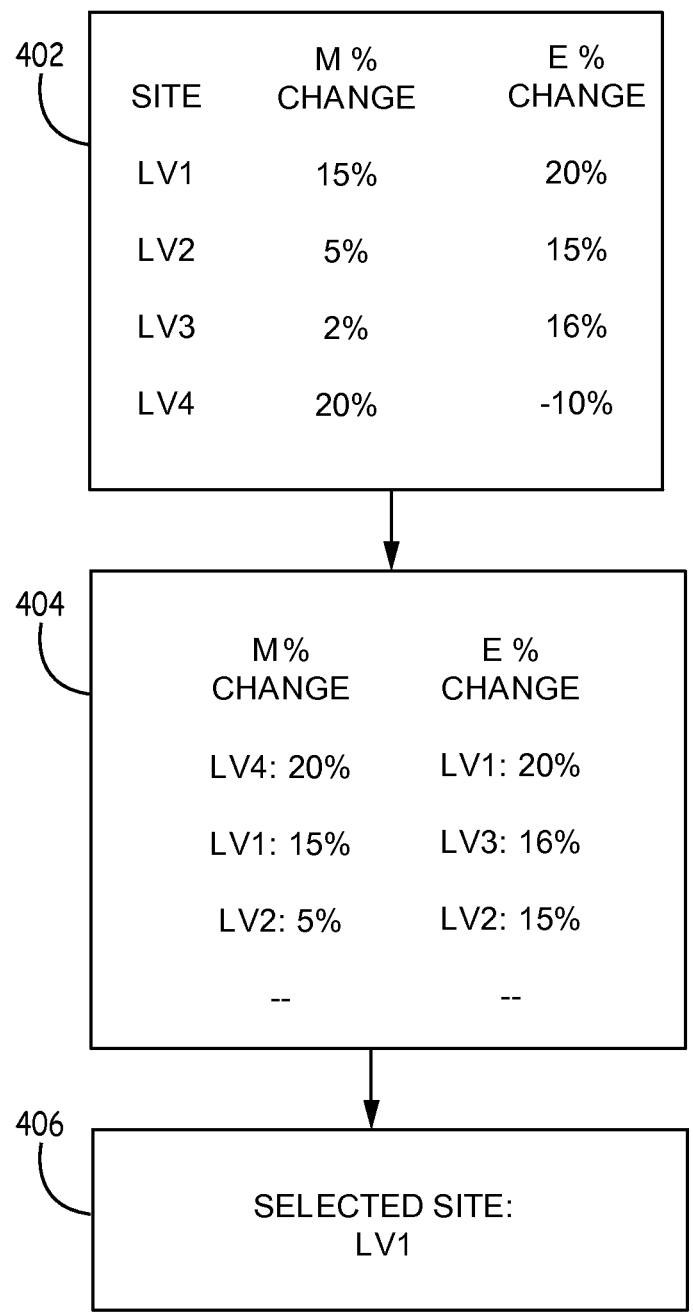
FIG. 4 depicts an example ordering of mechanical and electrical synchrony indices.

FIG. 4 depicts an example ordering of mechanical and electrical synchrony indices. In this example, a positive percentage change in an index relative to a respective baseline represents an improvement in ventricular synchrony. A percentage change in the mechanical synchrony index (M % change) is listed for each of the four pacing sites LV1 through LV4 at electrodes 144a through 144d respectively. A percentage change in the electrical synchrony index (E % change) for each pacing site is also listed. Processor 80 determines these percentage changes 402 by comparing the indices determined by cardiac signal analyzer 90 for each test pacing episode to a respective baseline index stored in memory 82.

Processor 80 then sorts the percentage changes from greatest improvement in synchrony to least improvement in synchrony. The sorted lists 404 may eliminate pacing sites having a worsening in synchrony or not meeting a threshold improvement or a percentage of the maximum improvement measured for all pacing sites. In one example, if a maximum improvement in an index is 20%, pacing sites meeting at least half this improvement, or a 10% increase over the baseline will be sorted. Pacing sites resulting in less than half the maximum improvement will not be included in a sorted list.

In the example shown, pacing sites resulting in a negative change or less than 25% of the maximum improvement are not sorted. Therefore, LV4, resulting in a negative 10% change from baseline, is eliminated from the list of LV pacing sites ordered according to change in electrical synchrony index. LV3 is eliminated from the list of pacing sites ordered according to change in mechanical synchrony index because the 2% improvement from baseline is less than 25% of the maximum improvement of 20% (found during pacing at LV4).

In embodiments that perform test episodes including multi-site pacing, a higher threshold change requirement may be applied to multi-site combinations because of the additional power requirements (and subsequently shortened device longevity) associated with delivering multi-site pacing as compared to single site pacing in a given heart chamber. For example, if single pacing sites are required to meet at least 50% of a maximum improvement as given in the foregoing example, multi-site pacing combinations may be required to meet at least 110% of the maximum improvement determined for a single pacing site in order to justify the added power requirements of multi-site pacing for achieving increased clinical benefit.

The pacing sites common to both sorted lists 404 are LV1 and LV2. LV1 has a highest overall ranking since LV2 is ranked third out of three in both lists. Processor 80 produces a pacing site selection output 406 selecting LV1 as the therapy delivery pacing site because the greatest overall improvement in both electrical and mechanical synchrony is achieved. In various embodiments, a highest overall ranking may be determined by summing the ranking of each pacing site in the two lists and choosing the pacing site having the lowest sum. For example, the ranking of LV1 in position 2 for the sorted mechanical index list and in position 1 for the sorted electrical index list results in a summed ranking of 3, less than the summed ranking of 6 for LV2. A highest overall ranking may alternatively be determined as the sum of the percentage changes of the two indices for a given pacing site. The greatest sum indicates the optimal pacing site. The summed percentage increases is 35% for LV1 in this example and only 20% for LV2. Therefore, pacing site LV1 is selected as the LV pacing site during CRT.

Returning to flow chart 300 of FIG. 3, when pacing sites not meeting a minimum improvement threshold have been eliminated from the ordered lists, a common pacing site between the two lists may not exist. If no common pacing sites are included in the ordered lists as determined at block 320, alternative pacing site selection criteria are utilized at block 322 For example, the highest ranking site for mechanical synchrony index improvement may be selected which does not result in a worsening in the electrical synchrony index relative to baseline. Alternatively, a pacing site may be selected that results in the highest electrical synchrony index improvement and does not result in a worsening mechanical synchrony index relative to baseline. In this situation, a clinician preference may guide site selection in weighing mechanical vs. electrical synchrony improvement.

If only one common site is included in both ordered lists, that single common site is selected as the therapy delivery pacing site at block 326. If more than one pacing site is common to both ordered lists, an overall ranking of the common pacing sites is determined as described above in conjunction with FIG. 4. A highest ranking common pacing site is selected at block 326 as the pacing site for therapy delivery.

In embodiments that include testing of multi-site pacing, if a single pacing site is common to both lists, selection of a single site may be given preference to multi-site pacing to conserve battery life of the implanted device unless the multi-site pacing improvement is significantly greater than the single pacing site result. If multiple VV delays have been tested, a VV delay resulting in a highest overall ranking of the selected pacing site(s) is also selected for therapy delivery. As indicated previously, a pacing site may be selected from ordered lists generated separately for biventricular pacing and for LV only pacing. Furthermore, pacing sites may be selected from ordered lists generated separately for atrial pacing rhythms and for atrial sensing rhythms. Accordingly, at least four sets of ordered lists may be generated for biventricular pacing during atrial sensing and during atrial pacing and for LV-only pacing during atrial sensing and during atrial pacing to enable selection of optimal pacing site during each of these four types of pacing/heart rhythms.

At block 326, a selected pacing site may be coupled to the signal generator 84 via switching circuitry. Signal generator 84 may be enabled to deliver a pacing therapy according to programmed therapy delivery parameters stored in memory 82. Alternatively or additionally, a notification may be generated by processor 80 and transmitted by telemetry module 88 to external programmer 170 to notify a clinician of the recommended or automatically selected pacing site. A clinician may confirm the site selection before therapy delivery begins, however, site selection and therapy delivery may be performed automatically by IMD 10 without requiring user intervention in some embodiments.

Thus, various embodiments of a system and method for pacing site selection have been described. However, one of ordinary skill in the art will appreciate that various modifications may be made to the described embodiments without departing from the scope of the claims. For example, numerous indices of mechanical and electrical synchrony may be determined from various hemodynamic and electrical signals and used in the disclosed techniques for selecting a pacing site based on a combination of mechanical and electrical resynchronization. These and other examples are within the scope of the following claims.

The invention claimed is:

1. A method for selecting a pacing therapy site, comprising:
sensing baseline mechanical heart activity and baseline electrical heart activity;
storing the baseline mechanical heart activity and baseline electrical heart activity;
sensing mechanical heart activity and electrical heart activity during pacing at each of a plurality of pacing sites along a heart chamber;
storing the mechanical heart activity and electrical heart activity;
determining a change from the baseline mechanical heart activity to the sensed mechanical activity for each of the plurality of pacing sites along the heart chamber;
determining a change from the baseline electrical activity to the sensed electrical heart activity for each of the plurality of pacing sites along the heart chamber;
sorting the plurality of pacing sites in a first order based upon the changes in mechanical heart activity;
sorting the plurality of pacing sites in a second order based upon the changes in electrical heart activity; and
selecting a pacing site from the plurality of pacing sites as a common pacing site between the first order and the second order.

2. The method of claim 1, further comprising rejecting a pacing site from the first order resulting in a change in the mechanical heart activity not meeting a threshold change.

3. The method of claim 1, further comprising rejecting a pacing site from the second order resulting in a change in the electrical heart activity not meeting a threshold change.

4. The method of claim 1, further comprising rejecting a pacing site from the first order and the second order in response to the pacing site not meeting one of a threshold change in mechanical activity and a threshold change in electrical activity.

5. The method of claim 1, further comprising selecting a pacing site from the first order and the second order having an overall highest ranking in the first order and the second order when more than one pacing site is common to the first order and the second order.

6. The method of claim 5, further comprising:
- determining an overall ranking of each pacing site by summing a ranking in the first order and a ranking in the second order for each pacing site; and
- identifying the overall highest ranking in response to the overall rankings.

7. The method of claim 5, further comprising:
- determining an overall ranking of each pacing site by summing a proportional change in the first order and a proportional change in the second order for each pacing site; and
- identifying the overall highest ranking in response to the overall rankings.

8. The method of claim 1, further comprising:
- determining whether a change exists between the baseline mechanical activity and the mechanical heart activity for each of a plurality of test episodes defined by a combination of one of the plurality of pacing sites and one of a plurality of pacing intervals;
- determining whether a a change exists from a baseline electrical activity and electrical activity during each of the plurality of test episodes;
- sorting the plurality of test episodes in a first order based upon the changes in mechanical heart activity;
- sorting the plurality of test episodes in a second order based upon the changes in electrical heart activity; and
- selecting a pacing site from the plurality of pacing sites as a common pacing site between the first order and the second order and selecting a pacing interval resulting in a highest overall ranking of the pacing site.

9. The method of claim 1, further comprising generating a notification of a selected pacing site.

10. The method of claim 1, further comprising delivering cardiac resynchronization therapy using the selected pacing site.

11. A medical device system for selecting a pacing therapy site, comprising:
- a plurality of electrodes configured to produce a signal of electrical heart activity and for delivering cardiac pacing pulses to a plurality of pacing sites along a heart chamber;
- a sensor for producing a signal of mechanical heart activity;
- a processor means for determining baseline mechanical heart activity from the sensor signal and baseline electrical heart activity from the signal of electrical heart activity, determining from the signal of mechanical heart activity a change from the baseline mechanical heart activity during pacing at each of the plurality of pacing sites and for determining from the signal of electrical heart activity a change from the baseline electrical activity during pacing at each of the plurality of pacing sites;
- a processor sorting means for sorting the plurality of pacing sites in a first order based upon the changes in mechanical heart activity and in a second order based upon the changes in electrical heart activity; and
- a processor selecting means for selecting a pacing site from the plurality of pacing sites as a common pacing site between the first order and the second order.

12. The system of claim 11, wherein the processor sorting means rejects a pacing site from the first order resulting in a change in the mechanical heart activity not meeting a threshold change.

13. The system of claim 11, wherein the processor sorting means rejects a pacing site from the second order resulting in a change in the electrical heart activity not meeting a threshold change.

14. The system of claim 11, wherein the processor sorting means rejects a pacing site from the first order and the second order in response to the pacing site not meeting one of a threshold change in mechanical activity and a threshold change in electrical activity.

15. The system of claim 11, wherein the processor selecting means selects a pacing site from the first order and the second order having an overall highest ranking in the first order and the second order when more than one pacing site is common to the first order and the second order.

16. The system of claim 15, wherein the processor selecting means determines an overall ranking of each pacing site by summing a ranking in the first order and a ranking in the second order for each pacing site and identifies the overall highest ranking in response to the overall rankings.

17. The system of claim 15, further comprising:
- wherein the processor selecting means determines an overall ranking of each pacing site by summing a proportional change in the first order and a proportional change in the second order for each pacing site and identifies the overall highest ranking in response to the overall rankings.

18. The system of claim 11, wherein the processor means for determining comprises processing means for extracting baseline mechanical heart activity from the sensor signal and baseline electrical activity from the signal of electrical heart activity,
- determining whether a change exists from the baseline mechanical activity to the mechanical activity for each of a plurality of test episodes defined by a combination of one of the plurality of pacing sites and one of a plurality of pacing intervals and
- determining whether a change exists from the baseline electrical activity to electrical activity sensed during each of the plurality of test episodes;
- wherein the processor sorting means sorts the plurality of test episodes in a first order based upon the changes in mechanical heart activity and in a second order based upon the changes in electrical heart activity; and
- the processor selecting means selects a pacing site from the plurality of pacing sites as a common pacing site between the first order and the second order and selects a pacing interval resulting in a highest overall ranking of the pacing site.

19. The system of claim 11, further comprising a processor generating means for generating a notification of a selected pacing site.

20. The system of claim 11, further comprising a cardiac signal generator for delivering cardiac resynchronization therapy using the selected pacing site.

21. A non-transitory, computer-readable storage medium comprising instructions that, when executed, cause a processor included in a medical device system to:
- sense baseline mechanical heart activity and baseline electrical heart activity;
- store the baseline mechanical heart activity and baseline electrical heart activity;
- sense mechanical heart activity and electrical heart activity during pacing at each of a plurality of pacing sites along a heart chamber;
- store the mechanical heart activity and electrical heart activity;
- determine a change from the baseline mechanical heart activity to the sensed mechanical heart activity for each of the plurality of pacing sites along the heart chamber;

determine a change from the baseline electrical activity to the sensed electrical heart activity during pacing at each of the plurality of pacing sites in the heart chamber;

sort the plurality of pacing sites in a first order based upon changes in mechanical heart activity and in a second order based upon changes in electrical heart activity; and select a pacing site from the plurality of pacing sites as a common pacing site between the first order and the second order.

22. An apparatus for selecting a pacing therapy site, comprising:

processing means for determining from a signal of mechanical heart activity a change from a previously determined baseline mechanical activity during pacing at each of a plurality of pacing sites along a heart chamber;

processing means for determining from a signal of electrical heart activity a change from a previously determined baseline electrical activity during pacing at each of the plurality of pacing sites along the heart chamber;

sorting means for sorting the plurality of pacing sites in a first order based upon the changes in mechanical heart activity;

sorting means for sorting the plurality of pacing sites in a second order based upon the changes in electrical heart activity; and processing means selecting a pacing site from the plurality of pacing sites as a common pacing site between the first order and the second order.

* * * * *